(12) United States Patent
Fulford

(10) Patent No.: US 6,500,394 B1
(45) Date of Patent: Dec. 31, 2002

(54) DRY STERILIZER

(75) Inventor: Tony Fulford, Mt. Airy, MD (US)

(73) Assignee: Cellpoint Scientific, Inc., Rockville, MD (US)

( * ) Notice: Subject to any disclaimer, the term of this patent is extended or adjusted under 35 U.S.C. 154(b) by 0 days.

(21) Appl. No.: 09/343,713

(22) Filed: Jun. 30, 1999

(51) Int. Cl.[7] ................................................ A61L 2/04
(52) U.S. Cl. ........................ 422/307; 219/201; 219/385; 219/521
(58) Field of Search ........................... 422/1, 297, 300, 422/307; 219/201, 521, 385

(56) References Cited

U.S. PATENT DOCUMENTS

| | | | | |
|---|---|---|---|---|
| 1,433,388 A | * | 10/1922 | Ledig | 422/307 |
| 3,898,045 A | * | 8/1975 | Bowley | 422/307 |
| 4,124,122 A | * | 11/1978 | Emmitt | 422/104 |
| 4,896,023 A | * | 1/1990 | Uchiyama | 219/521 |
| 5,265,890 A | * | 11/1993 | Balsells | 277/163 |
| 5,396,049 A | * | 3/1995 | Knopf | 422/307 |

OTHER PUBLICATIONS

Dental Catalog, Henry Schein Inc. 1978, p. 154.*
"The Pulpdent Glass Bead Sterilizer" Pulpdent Corporation of America, 1986.
Dental Catalog, Henry Schein Inc., 1978, p. 154.
Instrument Sterilizer dry, glass bead, Roboz Surgical, Prior Art.

* cited by examiner

Primary Examiner—Elizabeth McKane
(74) Attorney, Agent, or Firm—Leydig, Voit & Mayer, Ltd.

(57) ABSTRACT

A dry sterilizer includes a container for containing beads, a heater, and a resilient member disposed adjacent to an opening of the container. An instrument, after sterilization, is tapped against the resilient member to remove beads attached to and lodged in the instrument and the removed beads are returned to the container. The resilient member prevents beads from entering a housing of the sterilizer by blocking a gap between the container and the housing at the opening.

4 Claims, 1 Drawing Sheet

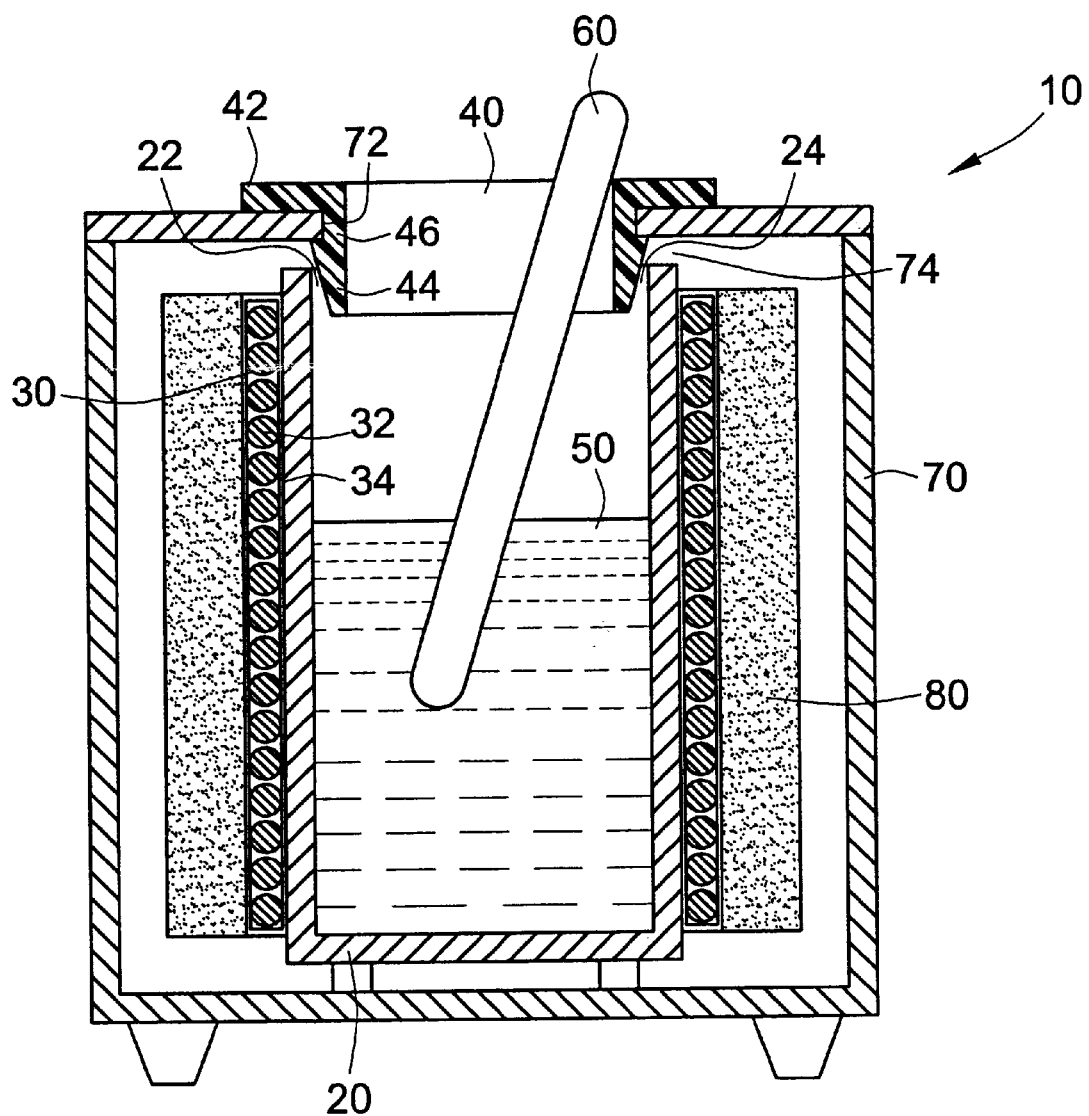

DRY STERILIZER

FIELD OF THE INVENTION

This invention relates to a dry sterilizer for decontaminating instruments.

BACKGROUND OF THE INVENTION

A dry sterilizer is used to decontaminate, i.e., sterilize for limited purposes, parts of instruments. In the dry sterilizer, a part of an instrument is immersed in a reservoir of heated inert beads, such as glass beads, and sterilizing heat is transferred from the beads to the instrument. The immersed part of the instrument is decontaminated after it has been heated to or above a sufficient temperature for a sufficient period of time, for example, 500° F. for at least 15 seconds. A dry sterilizer can be used to decontaminate a variety of parts of instruments such as the tip of a scalpel or the tips of scissors, forceps, or tweezers.

In the dry sterilization process, some of the beads may become attached to or lodge in an instrument after the instrument has been decontaminated. Removing the beads can be a time-consuming process. For example, a probe may have to be used to dislodge beads from the instrument with possible contamination of the instrument by the probe. The beads removed from the instrument may not be returned to the dry sterilizer and contaminate a working area so that beads may have to be added to the bead reservoir to compensate for lost beads.

The beads have to be replaced from time to time. The known dry sterilizers generally have a gap between a container for the beads and a housing of the sterilizer to limit the transfer of heat to the housing. Removing the old beads and adding beads can result in beads falling through the gap and being trapped within the housing, clogging or fouling the interior of the sterilizer.

SUMMARY OF THE INVENTION

This invention provides a dry sterilizer that overcomes drawbacks associated with conventional dry sterilizers.

In accordance with one aspect of the invention, a dry sterilizer includes a container for containing beads and having an opening, a heater, and a resilient member disposed opposite the opening of and providing access to the container. The resilient member supports an instrument being decontaminated and, after decontamination, provides for tapping of the instrument to remove any beads attached to and lodged in the instrument, without damaging the instrument, and for returning the beads in the container. In addition, the resilient member blocks a gap between the housing and the container preventing beads from falling between the housing and the container when the beads are changed or an instrument cleaned. Since the member has a relatively low thermal conductivity, the housing does not become excessively warm even if the member provides a thermal bridge between the housing and the container.

BRIEF DESCRIPTION OF THE DRAWINGS

The FIGURE is a cross-sectional view of a dry sterilizer according to an embodiment of the invention.

DETAILED DESCRIPTION OF THE PREFERRED EMBODIMENTS

The FIGURE illustrates an embodiment of a dry sterilizer 10 according to the invention. The dry sterilizer 10 includes a container 20 having an opening 22, a heater 30 for heating the container 20, and a resilient member 40 disposed opposite the opening 22 of the container 20 and providing access to the container. In the illustrated embodiment, the container 20 includes a circular opening 22 for adding and removing beads and providing access for an instrument 60. The container 20 holds inert beads 50 that are heated by the heater 30. The heater 30 is preferably an electric heater having one or more resistance wires or strips 32 enclosed in a casing 34 surrounded by thermal insulation 80. The heater 30 maintains the beads 50 at a temperature, such as 500° F., sufficient for decontaminating instruments. A part of the instrument 60 can be decontaminated by immersion in the heated beads 50 for a sufficient period of time, for example, at least 15 seconds. Having been decontaminated, the instrument 60 may be drawn along and/or tapped against the member 40 to remove any beads attached to and lodged in the instrument 60. The dry sterilizer 10 also includes a housing 70, thermal insulation 80, a temperature regulator (not shown), a temperature sensor (not shown), a switch (not shown), and a pilot light (not shown). The housing 70 supports and is partially spaced from the container to provide additional thermal insulation from the container 20 and the heater 30 to protect a user. The housing 70 has an opening 72 directly opposite and aligned with, but spaced from the opening 22 of the container 20 and spaced from the container 20.

The resilient member 40 is made of a soft, yielding material, such as a plastic, and is firmly mounted in the opening 72 of the housing 70, providing the only access to the container 20. Preferably, the resilient member 40 is slippery and has a smooth surface so that beads do not adhere to it. Further, the resilient member 40 has a relatively low thermal conductivity.

In the FIGURE, the resilient member 40 has a generally annular configuration but may have another configuration, such as a polygonal configuration. Although the resilient member 40 is shown attached to the housing 70, it may be attached to the container 20 or to both the container 20 and the housing 70. The member 40 can be attached to the housing or container by friction, an adhesive, or a fastener, such as one or more clamps, bolts, or screws.

In the embodiment shown in the FIGURE, the resilient member 40 has a generally annular, i.e., tubular, configuration with a radially outwardly extending flange 42 at one end, contacting the outside surface of the housing 70. At the other end, the resilient member 40 includes a portion 44 having a tapered thickness. The resilient member 40 includes an annular groove 46 between the flange 42 and the tapered portion 44 receiving the edge of the opening 72 of the housing 70. The resilient member 40 may be attached to the housing 70 by deforming the member slightly and urging the tapered portion 44 of the member 40 through the opening 72. The portion 44 is smaller in area and dimensions than the opening 22 of the container 20 so that beads falling through the resilient member 40 drop into the container 20. The member is preferably long enough, between the flange 42 and portion 44, to block any gap 74 between the housing 70 and the container 20. Thus, the resilient member 40 prevents beads from entering the space between the housing 70 and the container 20. The beads are prevented from entering that space during replacement of the beads or during dislodging of beads from an instrument.

The resilient member 40 can be made of any suitable material that does not break when an instrument is tapped against it and is sufficiently resilient so that an instrument is not damaged when it is tapped against the member. In addition, the material should have a low thermal conductivity so that heat radiated from or conducted from the container 20 does not unduly raise the temperature of the housing 70. That temperature should be low enough to avoid burns and undue response if the housing is touched. Preferred materials for the member include, but are not limited to, polyethylene, polytetrafluoroethylene, and like plastics that can withstand the heat of the sterilizer without deterioration.

What is claimed is:

1. A dry sterilizer comprising:

a housing having a top including an opening defined by an edge in the top;

a container for containing beads, disposed within the housing and having an opening, the container being disposed within the housing and spaced from the top at the opening of the container, the opening in the housing being located opposite the opening in the container;

a heater thermally coupled to the container for heating the beads in the container; and a plastic member mounted on the housing at the opening in the housing for supporting an instrument partially immersed in the beads of the housing and providing access to the opening in the container, wherein the plastic member extends between the top and the container to prevent the beads from passing between the housing and the container, the plastic member including a flange in contact with the top, a tubular portion extending from the flange, the tubular portion including a tapered part having a wall thickness increasing from an end opposite the flange toward the flange, and a circumferential groove between and defined by the flange and the tapered portion, the edge of the opening in the top being disposed within the groove, retaining the plastic member on the housing.

2. The dry sterilizer of claim 1, wherein the plastic member is annular.

3. The dry sterilizer of claim 1, wherein the plastic member is polytetrafluoroethylene.

4. The dry sterilizer of claim 1, wherein the plastic member is polyethylene.

* * * * *